(12) United States Patent
Takanezawa et al.

(10) Patent No.: US 7,471,758 B2
(45) Date of Patent: Dec. 30, 2008

(54) X-RAY CT APPARATUS

(75) Inventors: Hideaki Takanezawa, Nasushiobara (JP); Shinsuke Tsukagoshi, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 155 days.

(21) Appl. No.: 11/278,895

(22) Filed: Apr. 6, 2006

(65) Prior Publication Data

US 2006/0227929 A1    Oct. 12, 2006

(30) Foreign Application Priority Data

Apr. 7, 2005    (JP)    ............... 2005-111177

(51) Int. Cl.
  *H05G 1/60*    (2006.01)
  *G01N 23/00*    (2006.01)
(52) U.S. Cl. .................. 378/5; 378/4; 378/18
(58) Field of Classification Search .......... 378/4, 378/5, 18, 19, 109–112, 901; 382/131, 132
See application file for complete search history.

(56) References Cited

U.S. PATENT DOCUMENTS

| | | | |
|---|---|---|---|
| 6,631,284 B2 * | 10/2003 | Nutt et al. ................ 600/427 |
| 6,856,666 B2 * | 2/2005 | Lonn et al. ................ 378/8 |
| 7,031,426 B2 * | 4/2006 | Iatrou et al. ............... 378/5 |
| 7,272,429 B2 * | 9/2007 | Walker et al. ............. 600/407 |
| 2004/0030246 A1 * | 2/2004 | Townsend et al. ......... 600/427 |
| 2004/0101086 A1 * | 5/2004 | Sabol et al. ............... 378/4 |
| 2004/0202277 A1 | 10/2004 | Okumura et al. | |

FOREIGN PATENT DOCUMENTS

JP    2004-305527    11/2004

\* cited by examiner

*Primary Examiner*—Irakli Kiknadze
(74) *Attorney, Agent, or Firm*—Oblon, Spivak, McClelland, Maier & Neustadt, P.C.

(57) ABSTRACT

An X-ray CT apparatus comprising a storage device which stores therein a first table where fat contents are respectively associated with the values of the ratios of CT numbers, a CT number measurement unit which irradiates an object with X-rays under a plurality of different irradiation conditions, and which obtains actually-measured CT numbers for the respective irradiation conditions, and a fat content extraction unit which calculates the ratio of the actually-measured CT numbers for the respective irradiation conditions, and which extracts the fat content corresponding to the ratio of the actually-measured CT numbers, by referring to the first table.

13 Claims, 11 Drawing Sheets

| FAT CONTENTS (%) | SAMPLE CT NUMBERS | | NUMBERS OF FAT FACTOR ($^{120}C / {}^{100}C$) |
|---|---|---|---|
| | 120 (kV) | 100 (kV) | |
| 10 | $^{120}C_{10\%}$ | $^{100}C_{10\%}$ | NUMBER OF ($^{120}C_{10\%} / {}^{100}C_{10\%}$) = $\alpha$ |
| 20 | $^{120}C_{20\%}$ | $^{100}C_{20\%}$ | NUMBER OF ($^{120}C_{20\%} / {}^{100}C_{20\%}$) = $\beta$ |
| 30 | $^{120}C_{30\%}$ | $^{100}C_{30\%}$ | NUMBER OF ($^{120}C_{30\%} / {}^{100}C_{30\%}$) = $\gamma$ |
| 40 | $^{120}C_{40\%}$ | $^{100}C_{40\%}$ | NUMBER OF ($^{120}C_{40\%} / {}^{100}C_{40\%}$) = $\delta$ |
| 50 | $^{120}C_{50\%}$ | $^{100}C_{50\%}$ | NUMBER OF ($^{120}C_{50\%} / {}^{100}C_{50\%}$) = $\varepsilon$ |
| 60 | $^{120}C_{60\%}$ | $^{100}C_{60\%}$ | NUMBER OF ($^{120}C_{60\%} / {}^{100}C_{60\%}$) = $\zeta$ |

FIG. 4

| WATER-EQUIVALENT THICKNESSES | SAMPLE CT NUMBERS | |
|---|---|---|
| | 120 (kV) | 100 (kV) |
| 180 | $^{120}C_{180}$ | $^{100}C_{180}$ |
| 240 | $^{120}C_{240}$ | $^{100}C_{240}$ |
| 320 | $^{120}C_{320}$ | $^{100}C_{320}$ |
| 400 | $^{120}C_{400}$ | $^{100}C_{400}$ |

FIG. 5

| FAT CONTENTS(%) | SAMPLE CT NUMBERS | | NUMBERS OF FAT FACTOR ($^{120}C-^{80}C$) |
| --- | --- | --- | --- |
| | 120 (kV) | 80 (kV) | |
| 2 | $^{120}C_{2\%}$ | $^{80}C_{2\%}$ | NUMBER OF $(^{120}C_{2\%} - {}^{80}C_{2\%}) = \eta$ |
| 5 | $^{120}C_{5\%}$ | $^{80}C_{5\%}$ | NUMBER OF $(^{120}C_{5\%} - {}^{80}C_{5\%}) = \theta$ |
| 8 | $^{120}C_{8\%}$ | $^{80}C_{8\%}$ | NUMBER OF $(^{120}C_{8\%} - {}^{80}C_{8\%}) = \iota$ |
| 10 | $^{120}C_{10\%}$ | $^{80}C_{10\%}$ | NUMBER OF $(^{120}C_{10\%} - {}^{80}C_{10\%}) = \kappa$ |
| 15 | $^{120}C_{15\%}$ | $^{80}C_{15\%}$ | NUMBER OF $(^{120}C_{15\%} - {}^{80}C_{15\%}) = \lambda$ |
| 20 | $^{120}C_{20\%}$ | $^{80}C_{20\%}$ | NUMBER OF $(^{120}C_{20\%} - {}^{80}C_{20\%}) = \mu$ |

FIG. 11

X-RAY CT APPARATUS

BACKGROUND OF THE INVENTION

1. Field of the Invention

The present invention relates to a technique which generates an image within an object, on the basis of a projection data obtained by irradiating the object with X-rays. More particularly, it relates to an X-ray CT apparatus which quantifies a fat content in a predetermined region, from such an image.

2. Description of the Related Art

The progress of a X-ray CT (Computed Tomography) apparatuses in recent years is remarkable. In compliance with the eager desire of medical treatment sites to radiograph a human body or the like at a higher precision (resolution) and in a wider range, a multislice X-ray CT apparatus has been developed and has come into considerably wide use. The multislice X-ray CT apparatus is configured including an X-ray source which irradiates an object with cone beam X-rays having a spread width in a slice direction (a lengthwise direction of a table-top), and a two-dimensional detector in which a plurality of detection element rows are arrayed in a slice direction, whereby helical scan can be performed. Thus, as compared with a single-slice X-ray CT apparatus, the multislice X-ray CT apparatus can obtain volume data over a wider range within an object, at a higher precision and in a shorter time.

With such an X-ray CT apparatus in the prior art, in a case, for example, where the liver part of a patient has been radiographed, the advanced degree of fatty liver is sometimes judged from the visual impression of a diagnostician for an obtained image, a CT number measurement based on a region of interest (ROI), or the like. The judgment of the advanced degree of the fatty liver, however, depends greatly on the subjectivity of the diagnostician.

Besides, measured the CT number tend to involve a size-dependency in accordance with the discrepancy of the physique of the patient. Therefore, it cannot be always said an appropriate diagnosis to judge the advanced degree of the fatty liver on the basis of the CT number measured without taking the physique of the patient into consideration.

SUMMARY OF THE INVENTION

The present invention has taken into consideration the above-described problems, and it is an object of the present invention to provide a X-ray CT apparatus such that a fat content of a region of interest can be objectively quantified and displayed from a CT number which have been measured on the basis of an image information obtained by employing the X-ray CT apparatus.

To solve the above-described problems, the present invention provides a X-ray CT apparatus, comprising: a storage device which stores therein a first table where a fat content is respectively associated with a value of a ratio of CT numbers; a CT number measurement unit which irradiates an object with X-rays under different irradiation conditions, and which obtains actually-measured CT numbers for the plurality of different irradiation conditions; and a fat content extraction unit which calculates a ratio of the actually-measured CT numbers every the different irradiation conditions, and which extracts the fat content corresponding to the ratio of the actually-measured CT numbers, by referring to the first table.

To solve the above-described problems, the present invention provides a X-ray CT apparatus, comprising: a first storage device which previously stores therein a first table where a fat content and a ratio of sample CT numbers of desired water phantoms for different irradiation conditions are associated with each other, the sample CT numbers having been obtained in such a way that the water phantoms containing predetermined quantities of fats were irradiated with X-rays under the different irradiation conditions; a second storage device which previously stores therein a second table where sample CT numbers at respective water-equivalent thicknesses of water phantoms of different sizes are stored for the different irradiation conditions; a CT number measurement unit which irradiates an object with X-rays under the different irradiation conditions, and which obtains actually-measured CT numbers for the different respective irradiation conditions; a size measurement unit which measures a water-equivalent thickness of the object; a size-dependent correction unit which calculates size-dependent correction coefficients based on the sizes of the desired water phantoms and the water-equivalent thickness of the object as has been measured by said size measurement unit, by referring to the second table, and which corrects the actually-measured CT numbers by multiplying the actually-measured CT numbers by the size-dependent correction coefficients of the same irradiation conditions; a fat factor calculation unit which calculates a ratio of the actually-measured CT numbers corrected by said size-dependent correction unit, as a fat factor; and a fat content extraction unit which extracts the fat content corresponding to the fat factor, by referring to the first table.

To solve the above-described problems, the present invention provides a X-ray CT apparatus, comprising: a storage device which stores therein a first table where a fat content is respectively associated with a value of a difference of CT numbers; a CT number measurement unit which irradiates an object with X-rays under different irradiation conditions, and which obtains actually-measured CT numbers for the different irradiation conditions; and a fat content extraction unit which calculates a difference of the actually-measured CT numbers for the plurality of different irradiation conditions, and which extracts the fat content corresponding to the difference of the actually-measured CT numbers, by referring to the first table.

To solve the above-described problems, the present invention provides a X-ray CT apparatus, comprising: a first storage device which previously stores therein a first table where a fat content and a difference of sample CT numbers of desired water phantoms for different irradiation conditions are associated with each other, the sample CT numbers having been obtained in such a way that the water phantoms containing predetermined quantities of fats were irradiated with X-rays under the different irradiation conditions; a second storage device which previously stores therein a second table where sample CT numbers at respective water-equivalent thicknesses of water phantoms of different sizes are stored for the different irradiation conditions; a CT number measurement unit which irradiates an object with X-rays under the different irradiation conditions, and which obtains actually-measured CT numbers for the different respective irradiation conditions; a size measurement unit which measures a water-equivalent thickness of the object; a size-dependent correction unit which calculates size-dependent correction coefficients based on the sizes of the desired water phantoms and the water-equivalent thickness of the object as has been measured by said size measurement unit, by referring to the second table, and which corrects the actually-measured CT numbers by multiplying the actually-measured CT numbers by the size-dependent correction coefficients of the same irradiation conditions; a fat factor calculation unit which calculates a difference of the actually-measured CT numbers corrected by said size-dependent correction unit, as a fat factor; and a fat content extraction unit which extracts the fat content corresponding to the fat factor, by referring to the first table.

To solve the above-described problems, the present invention provides a X-ray CT apparatus, comprising: a storage device which stores therein a conversion formula that has been calculated on the basis of fat contents versus values of differences of CT numbers; a CT number measurement unit which irradiates an object with X-rays under different irradiation conditions, and which obtains actually-measured CT numbers for the different irradiation conditions; and a fat content conversion unit which calculates the difference of the actually-measured CT numbers for the respective irradiation conditions, and which converts the difference of the actually-measured CT numbers into the fat content, by referring to the conversion formula.

To solve the above-described problems, the present invention provides a X-ray CT apparatus, comprising: a storage device which stores therein a first table where fat contents are respectively associated with values of ratios of CT numbers; a CT number measurement unit which irradiates an object with X-rays under a plurality of different irradiation conditions, and which obtains actually-measured CT numbers for the respective irradiation conditions; and a fat content extraction unit which calculates a comparative value of the actually-measured CT numbers for the respective irradiation conditions, and which extracts the fat content corresponding to the comparative value of the actually-measured CT numbers, by referring to the first table.

The X-ray CT apparatus as described above makes the fat content of the region of interest possible to be objectively quantified and displayed from the CT number which have been measured on the basis of the image information obtained by employing the X-ray CT apparatus.

BRIEF DESCRIPTION OF THE DRAWINGS

In the accompanying drawings:

FIG. 4 is a diagram showing an example of the first table;

FIG. 5 is a diagram showing an example of a second table;

FIG. 11 is a diagram showing an outline for obtaining the fat content conversion formula;

DESCRIPTION OF THE PREFERRED EMBODIMENTS

A preferred embodiments of a X-ray CT apparatus according to the present invention will be described with reference to the accompanying drawings.

Figure 1:
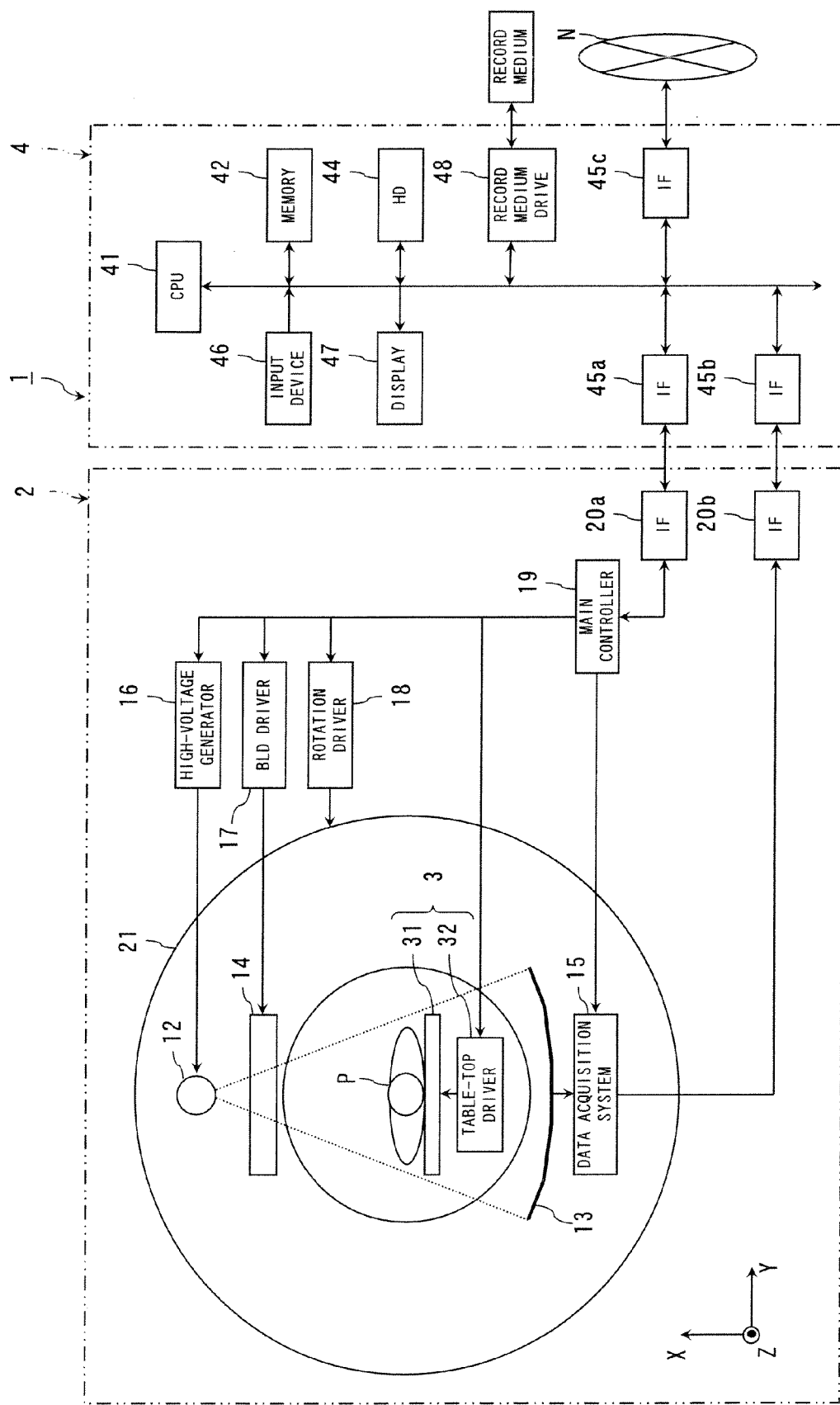
FIG. 1 is a block diagram showing the hardware architecture of an X-ray CT apparatus.

FIG. 1 is a block diagram showing a hardware architecture of an X-ray CT apparatus.

FIG. 1 shows a X-ray CT apparatus 1, which includes a gantry system 2 configured for acquiring data on an object (patient) P, a table system 3 for carrying and moving the patient P, and an operation console 4 for inputting data and displaying an image in order to operate the X-ray CT apparatus 1.

Mounted on the gantry system 2 of the X-ray CT apparatus 1 are an X-ray tube 12, an X-ray detector 13, a beam limiting device (abbreviated to "BLD") 14, a data acquisition system 15, a high-voltage generator 16, a BLD driver 17, a rotation driver 18, a main controller 19, an interface (IF) 20a, and an IF 20b.

Besides, the X-ray tube 12, X-ray detector 13, BLD 14 and data acquisition system 15 are located in a rotation section 21 of the gantry system 2. The rotation section 21 is configured so that the X-ray tube 12 and the X-ray detector 13 can be rotated round the patient P in a state where they are opposed to each other.

The X-ray tube 12 generates X-rays in accordance with a tube voltage fed from the high-voltage generator 16.

The X-ray detector 13 is a two-dimensional array type detector (also called "multislice type detector"). An X-ray detection element has a detection face that is, for example, 0.5 mm×0.5 mm square. In the X-ray detector 13, the X-ray detection elements numbering, for example, 916 are arrayed in a channel direction, and such arrays numbering, for example, at least 64 are juxtaposed along a slice direction (the row direction of the detector).

The BLD 14 adjusts the exposure range in the slice direction in which the patient P is irradiated with the X-rays, under the control of the BLD driver 17. That is, the X-ray exposure range in the slice direction can be altered by adjusting the aperture of the BLD 14 by the BLD driver 17.

The data acquisition system 15 is generally called "data acquisition system (DAS)", and it amplifies a signal outputted from the X-ray detector 13 every channel and further converts the signal into a digital signal. Data (raw data) after the conversion are supplied to the external operation console 4 through the IF 20b.

The main controller 19 controls the high-voltage generator 16, the BLD driver 17, the rotation driver 18 the data acquisition system 15 and the table system 3 on the basis of control signals inputted from the operation console 4 through the IF 20a.

The table system 3 of the X-ray CT apparatus 1 includes a table-top 31 on which the patient P is placed, and a table-top driver 32 which moves the table-top 31 along the slice direction. The rotation section 21 is centrally provided with an opening, in which the patient P placed on the table-top 31 is inserted. Incidentally, a direction parallel to the axis of rotation of the rotation section 21 is defined as a Z-axial direction (slice direction), and planes orthogonal to the Z-axial direction are respectively defined by an X-axial direction and a Y-axial direction.

The operation console 4 of the X-ray CT apparatus 1 is a so-called "workstation" which is configured on the basis of a computer, and which is intercommunicable with a network N such as hospital-centered LAN (Local Area Network). The operation console 4 is broadly configured of basic hardware items such as a central processing unit (CPU) 41, a memory 42, a hard disc (HD) 44, an IF 45a, an IF 45b, an IF 45c, an input device 46 and a display 47. The CPU 41 is interconnected to the individual hardware constituents constituting the operation console 4, through a bus which functions as a common signal transmission line. Incidentally, the operation console 4 sometimes includes a record medium drive 48.

When an instruction is inputted through the operation of the input device 46, or the like by a diagnostician such as a doctor, the CPU 41 runs a program stored in the memory 42. Alternatively, the CPU 41 loads a program into the memory 42 and runs the program, the program being one stored in the HD 44, one transferred from the network N and received by the IF 45c and then installed in the HD 44, or one read out from a record medium set in the record medium drive 48 and then installed in the HD 44.

The memory 42 is a storage device which serves as a read only memory (ROM), a random access memory (RAM) and the like elements, and which is used for storing an initial program loading (IPL), a basic input/output system (BIOS) and data, as the work memory of the CPU 41, and for temporarily storing data.

The HD 44 is configured of a nonvolatile semiconductor memory, or the like. This HD 44 is a storage device which stores therein programs (including application programs and also an operating system (OS), etc.) installed in the operation console 4, and data. Besides, the OS can be caused to offer a graphical user interface (GUI) which often employs graphics for the display of information to the diagnostician, and the basic operations of which can be performed by the input device 46.

The IF 45a, the IF 45b and the IF 45c perform communication controls which conform to respectively corresponding standards. The IF 45a and the IF 45b communicate with the gantry system 2, and are respectively connected to the IF 20a and the IF 20b of the gantry system 2. Besides, the IF 45c has a function capable of being connected to the network N through a telephone line, whereby the operation console 4 can be connected from the IF 45c to the network N.

The input device 46 is a pointing device that can be operated by the diagnostician, and an input signal conforming to the operation is sent to the CPU 41.

A monitor or the like is mentioned as the display 47. An image is displayed on the display 47 in such a way that image data to be displayed, etc. are expanded in a video random access memory (VRAM, not shown) or the like memory which expands the image data.

The record medium is detachably attached into the record medium drive 48. This record medium drive 48 reads out data (including the program) recorded in the record medium and outputs the data onto the bus, while it writes data supplied through the bus, into the record medium. Such a record medium can be offered as so-called "package software".

Figure 2:
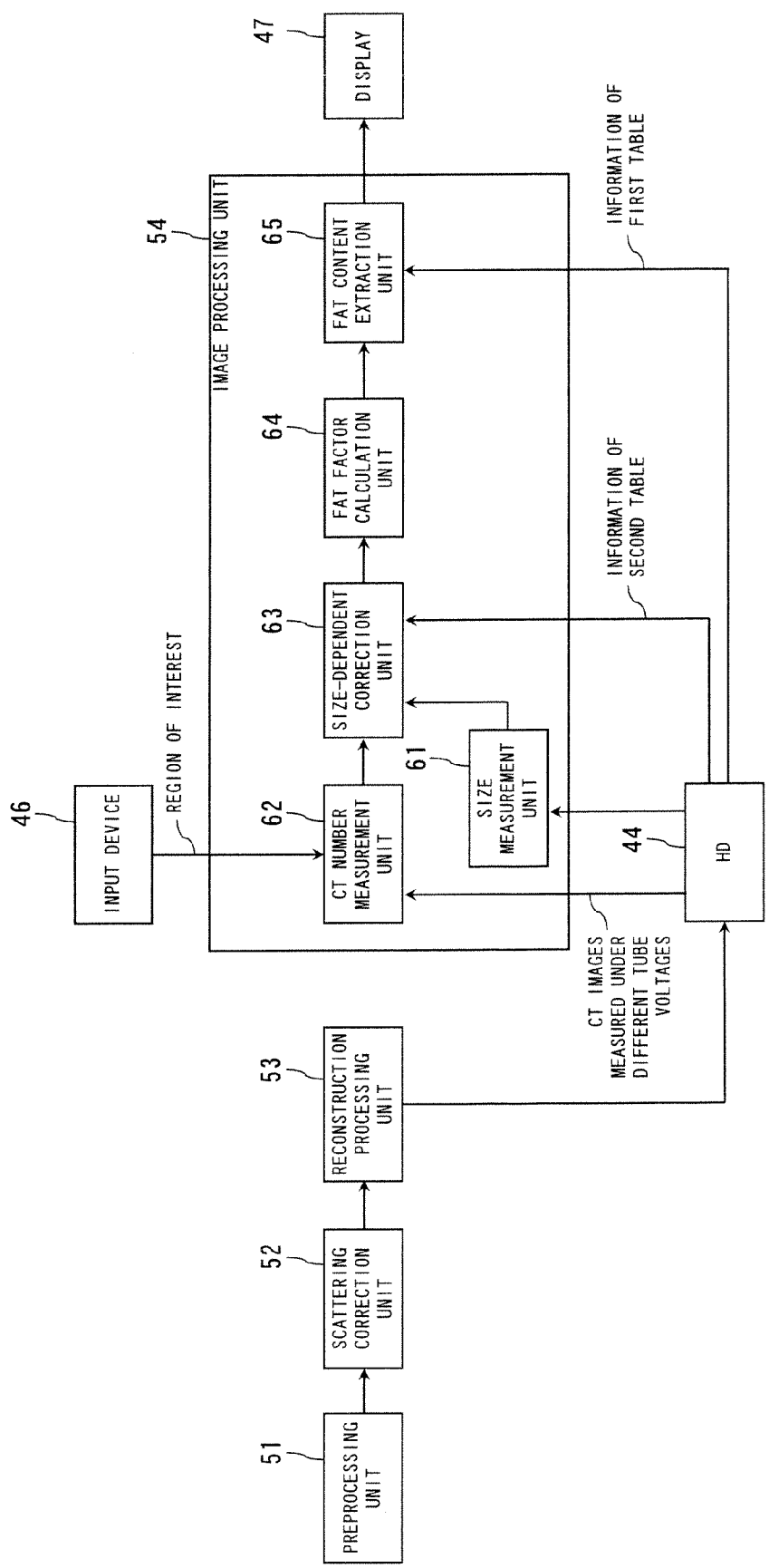
FIG. 2 is a block diagram showing a first embodiment of the X-ray CT apparatus according to the invention.

FIG. 2 is a block diagram showing the first embodiment of the X-ray CT apparatus according to the invention.

In the hardware architecture shown in FIG. 1, the CPU 41 of the operation console 4 of the X-ray CT apparatus 1 runs programs, whereby this operation console 4 functions as a preprocessing unit 51, a scattering correction unit 52, a reconstruction processing unit 53 and an image processing unit 54. Incidentally, the respective units 51 through 54 are assumed here to function in such a way that the CPU 41 runs the programs, but the invention is not restricted to that case. The respective units 51 through 54 may well be disposed in the operation console 4 as hardware.

The preprocessing unit 51 generates projection data in such a way that the raw data inputted from the data acquisition system 15 of the gantry system 2 through the IF 45b shown in FIG. 1 are subjected to correction processes such as a logarithmic conversion process and a sensitivity correction.

The scattering correction unit 52 subjects the projection data inputted from the preprocessing unit 51, to a process for removing scattered X-rays. This scattering correction unit 52 removes the scattered X-rays on the basis of the values of the projection data within the X-ray exposure range. A scattering correction is made in such a way that scattered X-rays estimated from the magnitudes of the values of the projection data being a subject for the scattering correction or projection data adjacent to the subject projection data are subtracted from the subject projection data. The projection data after the removal of the scattered X-rays are sent to the reconstruction processing unit 53.

The image reconstruction processing unit 53 reconstructs the image of "in-vivo" information within the patient P by employing a reconstruction method such as fan beam reconstruction for which it is assumed that X-ray paths in the slice direction are parallel, or cone beam reconstruction in which an X-ray exposure angle (cone angle) in the slice direction is considered.

The image processing unit 54 generates a display image in such a way that various items of image processing are executed for image data stored in the storage device such as HD 44. In order to generate the display image, the image processing unit 54 includes a size measurement unit 61, a CT number measurement unit 62, a size-dependent correction unit 63, a fat factor calculation unit 64 and a fat content extraction unit 65.

Here, a first table and a second table are stored in the storage device beforehand. The first table indicates the relationship between a fat content and the ratio of individual sample CT numbers measured under corresponding irradiation conditions, the relationship having been obtained in such a way that CT numbers under the plurality of different irradiation conditions were measured as the sample CT numbers, versus the fat content. On the other hand, the second table serves to correct an actually-measured CT number in accordance with the size of the patient P. Incidentally, the first table and the second table may well be stored in the separate storage devices.

Figure 3:
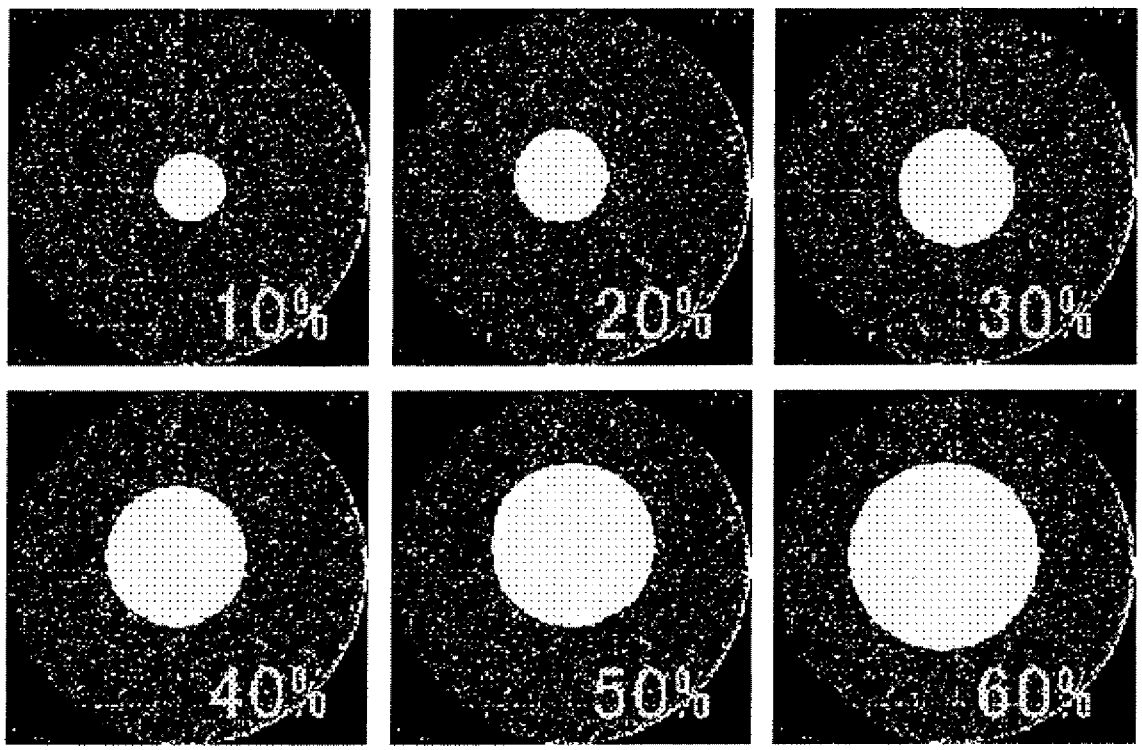
FIG. 3 is a diagram showing an outline for obtaining a first table.

FIG. 3 is a diagram showing an outline for obtaining the first table.

In order to obtain the first table at a preparatory stage before an examination, samples of various fat contents are first prepared, respectively. By way of example, the samples in which fats of weight-% values of 10%, 20%, 30%, 40%, 50% and 60% are mixed into water phantoms of predetermined quantity are respectively prepared. FIG. 3 shows images which have been obtained in such a way that the samples of the various fat contents were radiographed similarly to the ordinary patient P by employing the X-ray CT apparatus 1.

FIG. 4 is a diagram showing an example of the first table.

In the first table shown in FIG. 4, CT numbers obtained by measuring the samples of the various fat contents under different irradiation conditions, for example, tube voltages are indicated as sample CT numbers. By way of example, the sample CT number obtained by irradiating and measuring the sample of the fat content of 10% under the tube voltage of 120 kV is defined as $^{120}C_{10\%}$, while the sample CT number obtained by irradiating and measuring the same sample under the tube voltage of 100 kV is defined as $^{100}C_{10\%}$; the sample CT number obtained by irradiating and measuring the sample of the fat content of 20% under the tube voltage of 120 kV is defined as $^{120}C_{20\%}$, while the sample CT number obtained by irradiating and measuring the same sample under the tube voltage of 100 kV is defined as $^{100}C_{20\%}$; the sample CT number obtained by irradiating and measuring the sample of the fat content of 30% under the tube voltage of 120 kV is defined as $^{120}C_{30\%}$, while the sample CT number obtained by irradiating and measuring the same sample under the tube voltage of 100 kV is defined as $^{100}C_{30\%}$; the sample CT number obtained by irradiating and measuring the sample of the fat content of 40% under the tube voltage of 120 kV is defined as $^{120}C_{40\%}$, while the sample CT number obtained by irradiating and measuring the same sample under the tube voltage of 100 kV is defined as $^{100}C_{40\%}$; the sample CT number obtained by irradiating and measuring the sample of the fat content of 50% under the tube voltage of 120 kV is defined as $^{120}C_{50\%}$, while the sample CT number obtained by irradiating and measuring the same sample under the tube voltage of 100 kV is defined as $^{100}C_{50\%}$; and the sample CT number obtained by irradiating and measuring the sample of the fat content of 60% under the tube voltage of 120 kV is defined as $^{100}C_{60\%}$, while the sample CT number obtained by irradiating and measuring the same sample under the tube voltage of 100 kV is defined as $^{100}C_{60\%}$. Incidentally, although the case where the irradiation conditions are the tube voltages will be described below, the irradiation conditions are not restricted to the tube voltages, but they may well be, for example, tube currents (mA).

Besides, in the first table shown in FIG. 4, the fat contents and comparative values of the sample CT numbers measured under the plurality of different tube voltages are respectively associated with each other. In the first table the fat contents and comparative values of ratios of the sample CT numbers measured under the plurality of different tube voltages, for example, are respectively associated with each other. By way of example, the value α of the ratio of the sample CT numbers as is calculated from ($^{120}C_{10\%}/^{100}C_{10\%}$) is associated with the sample of the fat content of 10%, the value β of the ratio of the sample CT numbers as is calculated from ($^{120}C_{20\%}/^{100}C_{20\%}$) is associated with the sample of the fat content of 20%, the value γ of the ratio of the sample CT numbers as is calculated from ($^{120}C_{30\%}/^{100}C_{30\%}$) is associated with the sample of the fat content of 30%, the value δ of the ratio of the sample CT numbers as is calculated from ($^{120}C_{40\%}/^{100}C_{40\%}$) is associated with the sample of the fat content of 40%, the value δ of the ratio of the sample CT numbers as is calculated from ($^{120}C_{50\%}/^{100}C_{50\%}$) is associated with the sample of the fat content of 50%, and the value ξ of the ratio of the sample CT numbers as is calculated from ($^{120}C_{60\%}/^{100}C_{60\%}$) is associated with the sample of the fat content of 60%. By the way, in this embodiment, the different tube voltages were set at 120 kV and 100 kV as typical examples (tube currents were respectively held constant).

Further, as shown in FIG. 4, in this embodiment, the ratio of the sample CT numbers of the samples of each fat content is termed "fat factor". More specifically, in this embodiment, the tube voltages are made different to be 120 kV and 100 kV, as the different irradiation conditions. Therefore, the ratio between the sample CT number for the tube voltage of 120 kV and the sample CT number for the tube voltage of 100 kV is calculated, and each fat content is held in correspondence with the calculated result.

FIG. 5 is a diagram showing an example of the second table.

As shown in FIG. 5, the second table is a table which has been obtained in such a way that ordinary water phantoms were irradiated with X-rays, and that sample CT numbers corresponding to different water-equivalent thicknesses were measured under respective different irradiation conditions (for example, different tube voltages of 120 kV and 100 kV) with a predetermined FOV (Field Of View) of, for example, 400 mm. This table is for correcting that error of a CT number that develops depending upon the size of the patient P, in spite of the same irradiation condition and the same FOV.

By way of example, as shown in FIG. 5, in cases where the water-equivalent thicknesses of the water phantoms are 180 mm, 240 mm, 320 mm and 400 mm with the FOV=400 mm fixed, the sample CT numbers are measured for the tube voltages of 120 kV and 100 kV. Here, the sample CT number for the tube voltage of 120 kV and the water-equivalent thickness of 180 mm is defined as $^{120}C_{180}$, the sample CT number for the same tube voltage and the water-equivalent thickness of 240 mm is defined as $^{120}C_{240}$, the sample CT number for the same tube voltage and the water-equivalent thickness of 320 mm is defined as $^{120}C_{320}$, and the sample CT number for the same tube voltage and the water-equivalent thickness of 400 mm is defined as $^{120}C_{400}$. Likewise, the sample CT number for the tube voltage of 100 kV and the water-equivalent thickness of 180 mm is defined as $^{100}C_{180}$, the sample CT number for the same tube voltage and the water-equivalent thickness of 240 mm is defined as $^{100}C_{240}$, the sample CT number for the same tube voltage and the water-equivalent thickness of 320 mm is defined as $^{100}C_{320}$, and the sample CT number for the same tube voltage and the water-equivalent thickness of 400 mm is defined as $^{100}C_{400}$.

Besides, after the patient P has been irradiated with the X-rays at the stage of the examination, the size measurement unit 61 shown in FIG. 2 measures the size of the patient P on the basis of the scano data of the patient P as are stored in the storage device.

After the irradiation of the patient P with the X-rays, the CT number measurement unit 62 reads out the plurality of CT images of the patient P for the respective irradiation conditions, from the storage device. Besides, the CT number measurement unit 62 measures the actually-measured CT number obtained by averaging the CT numbers of the CT images read out of the storage device, for each of the irradiation conditions, with respect to the scano data of the patient P and on the basis of the region of interest which the diagnostician has inputted using the input device 46.

The size-dependent correction unit 63 subjects the actually-measured CT numbers obtained by the CT number measurement unit 62, to the corrections of the errors of the CT numbers as develop depending upon the size of the patient P, by referring to the second table.

Let's consider, for example, a case where the water-equivalent thickness of the water phantom on the occasion of creating the first table is 240 mm for the FOV=400 mm, and where the water-equivalent thickness of the patient P as has been measured for the region of interest by the size measurement unit 61 is 320 mm for the FOV=400 mm. The size-dependent correction unit 63 calculates a "corrected actually-measured CT number under the tube voltage of 120 kV" in such a way that the actually-measured CT number of the patient P as has been measured under the condition of the tube voltage of 120 kV by the CT number measurement unit 62 is multiplied by the value of the ratio ($^{120}C_{240}/^{120}C_{320}$) of the water-equivalent thicknesses as is obtained from the second table. On the other hand, the size-dependent correction unit 63 calculates a "corrected actually-measured CT number under the tube voltage of 100 kV" in such a way that the actually-measured CT number of the patient P as has been measured under the condition of the tube voltage of 100 kV by the CT number measurement unit 62 is multiplied by the value of the ratio ($^{100}C_{240}/^{100}C_{320}$) of the water-equivalent thicknesses as is obtained from the second table.

By the way, in this embodiment, the ratios of the water-equivalent thicknesses as indicated by ($^{120}C_{240}/^{120}C_{320}$) and ($^{100}C_{240}/^{100}C_{320}$) are defined as respective size-dependent correction coefficients. That is, in the above example, the size-dependent correction coefficient $^{120}k$ at the tube voltage of 120 kV is ($^{120}C_{240}/^{120}C_{320}$), and the size-dependent correction coefficient $^{100}k$ at the tube voltage of 100 kV is ($^{100}C_{240}/^{100}C_{320}$).

The fat factor calculation unit 64 shown in FIG. 2 calculates the ratio of the actually-measured CT numbers in the different irradiation conditions as have been obtained by the CT number measurement unit 62. The ratio is, for example, (actually-measured CT number under the tube voltage of 120 kV)/(actually-measured CT number under the tube voltage of 100 kV). When the corrections by the size-dependent correction unit 63 have been made, the ratio becomes (corrected actually-measured CT number under the tube voltage of 120 kV)/(corrected actually-measured CT number under the tube voltage of 100 kV).

The fat content extraction unit 65 extracts the fat content which corresponds to the value of the ratio of the actually-measured CT numbers or the value of the ratio of the corrected actually-measured CT numbers as has been obtained by the fat factor calculation unit 64, that is, a numerical value equivalent to the fat factor, by referring to the first table stored in the storage device. Besides, the fat content extracted by the fat content extraction unit 65 is displayed by the display 47, and it is quantitatively displayed as the objective fat content of the predetermined region in a scano image.

Figure 6:
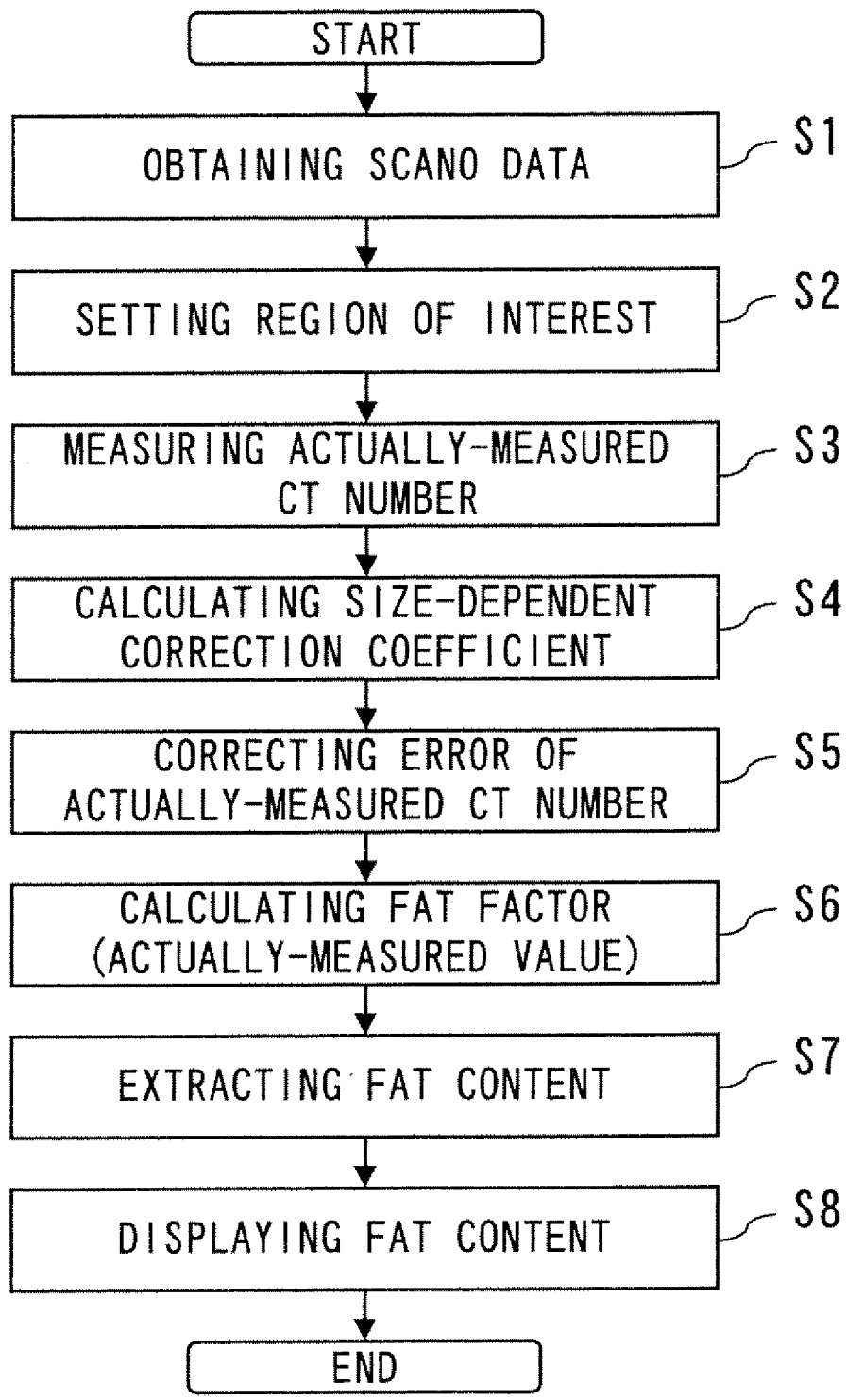
FIG. 6 is a an operation of the first embodiment of the X-ray CT apparatus according to the invention will be described with reference to a flow chart.

Next, the operation of the image processing unit 54 in the first embodiment of the X-ray CT apparatus according to the invention will be described with reference to a flow chart shown in FIG. 6.

First, after a reconstruction process has been ended by the reconstruction processing unit 53 shown in FIG. 2, the image processing unit 54 obtains scano data from the storage device such as HD 44 (step S1), and it causes the display 47 to display the scano data as a scano image.

Subsequently, the diagnostician designates a predetermined region for the scano image displayed on the display 47, whereby a region of interest is set (step S2).

Figure 7:
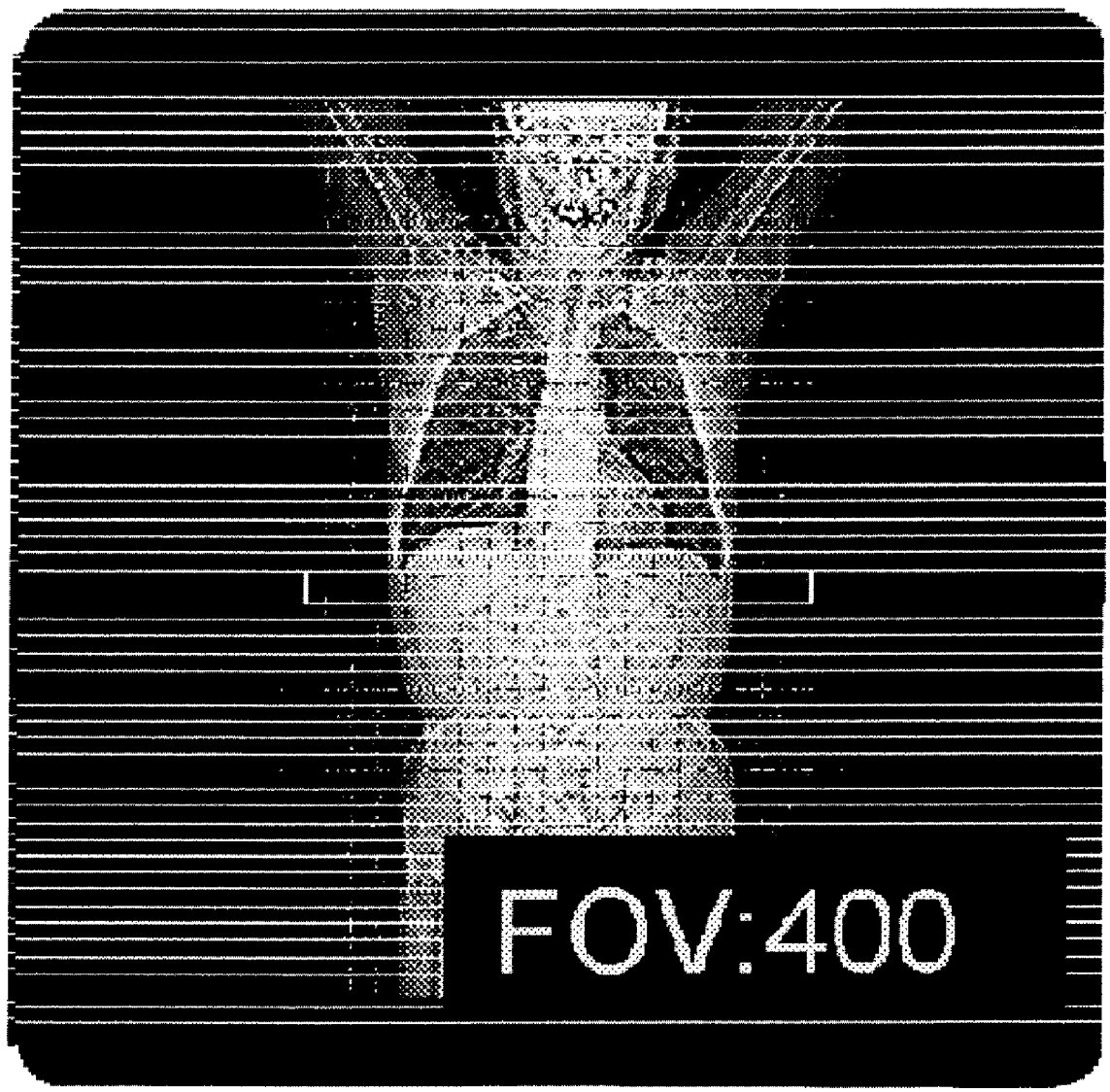
FIG. 7 is a diagram showing an example of a screen that contains the scano image, at the time when a predetermined region is designated.

FIG. 7 is a diagram showing an example of a screen that contains the scano image, at the time when the predetermined region is designated.

The designation of the predetermined region on the screen shown in FIG. 7 is done by processing coordinates on the scano data as have been specified using the input device 46 such as pointing device.

Next, the CT number measurement unit 62 shown in FIG. 2 measures an actually-measured CT number which is obtained by averaging CT numbers for each of different irradiation conditions, as to the region of interest set at the step S2 (step S3), and it causes the display 47 to display a CT image.

Figure 8:
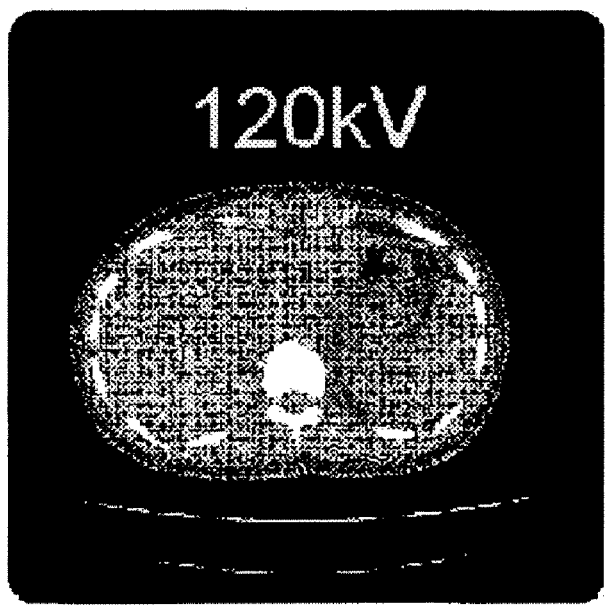
FIG. 8 is a diagram showing an example of a screen that contains a CT image, in the case of a tube voltage of 120 kV.
Figure 9:
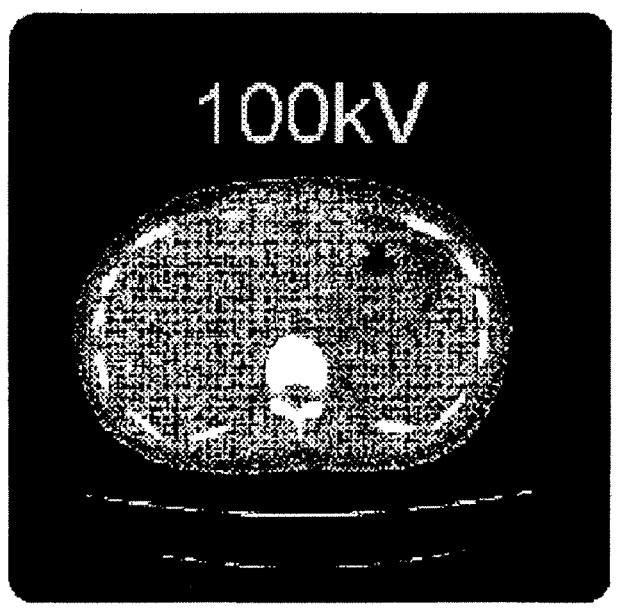
FIG. 9 is a diagram showing an example of a screen that contains a CT image, in the case of a tube voltage of 100 kV.

FIG. 8 is a diagram showing an example of a screen that contains the CT image, in the case of a tube voltage of 120 kV. On the other hand, FIG. 9 is a diagram showing an example of a screen that contains the CT image, in the case of a tube voltage of 100 kV.

Subsequently, the size-dependent correction unit 63 shown in FIG. 2 calculates a water-equivalent thickness within the region of interest set for the scano data at the step S2, and it calculates a size-dependent correction coefficient with reference to the second table (step S4).

Thereafter, the size-dependent correction unit 63 corrects the error of the actually-measured CT number attributed to the size of the patient P, in such a way that the actually-measured CT number of each irradiation condition is multiplied by the size-dependent correction coefficient calculated for the corresponding irradiation condition (step S5). By way of example, letting $C_{120}$ denote the CT actually-measured number within the region of interest at the tube voltage of 120 kV, and $C_{100}$ denote the mean CT actually-measured number within the region of interest at the tube voltage of 100 kV, a "corrected actually-measured CT number at the tube voltage of 120 kV" is evaluated as $C_{120} \times {}^{120}k$, and a "corrected actually-measured CT number at the tube voltage of 100 kV" is evaluated as $C_{100} \times {}^{100}k_{240}$ (as to $^{120}k$ and $^{100}k$, refer to the foregoing description).

Subsequently, using the "corrected actually-measured CT number at the tube voltage of 120 kV" and the "corrected actually-measured CT number at the tube voltage of 100 kV" evaluated by the size-dependent correction unit 63, the fat factor calculation unit 64 calculates the ratio of the corrected actually-measured CT numbers $((C_{120} \times {}^{120}k)/(C_{100} \times {}^{100}k))$ as a fat factor (actually-measured value) (step S6).

Besides, regarding the fat factor (actually-measured value) thus obtained, the fat content extraction unit 65 extracts a fat content associated with a fat factor (sample value) which indicates a substantially-agreeing numerical value, by referring to the first table stored in the storage device (step S7). In a case, for example, where the ratio $((C_{120} \times {}^{120}k)/(C_{100} \times {}^{100}k))$ which is the fat factor (actually-measured value) calculated by the fat factor calculation unit 64 is close to the fat factor γ indicated in the first table, a fat content "30%" is extracted from the first table. Incidentally, when the first table is referred to, the fat factor γ is a numerical value calculated by $^{120}C_{30\%}/^{100}C_{30\%}$).

Besides, in a case where the actually-measured fat factor is not close to any of the fat factors (α–ζ) being the sample values as indicated in FIG. 4, the fat content may well be obtained by interpolation.

The fat content extracted by the fat content extraction unit 65 is displayed by the display 47 so that the diagnostician can visually recognize this fat content (step S8). By way of example, a character string "Fat content of pertinent region is - - - %" is indicated in superposition on the display of the CT image.

Incidentally, this embodiment is a mere example of the invention, and the invention shall not be restricted to the configurations and operations described in this embodiment. Various alterations are possible in accordance with a design, etc., within a scope not departing from the technical idea according to the invention. By way of example, the fat factors indicated in the first table may well be replaced with the difference values between the sample CT numbers measured under the tube voltage of 120 kV and the sample CT numbers measured under the tube voltage of 100 kV. In that case, the size-dependent correction unit 63 evaluates corrected actually-measured CT numbers at the predetermined tube voltages, in such a way that the actually-measured CT numbers of the patient P as have been measured under the tube voltages of 120 kV and 100 kV are multiplied by the difference values of the water-equivalent thicknesses obtained from the second table.

In accordance with the image processing unit 54 of the X-ray CT apparatus 1 according to the invention, the fat content of the region of interest can be objectively quantified and displayed from the CT numbers which have been measured on the basis of the image information obtained by employing the X-ray CT apparatus 1.

Figure 10:
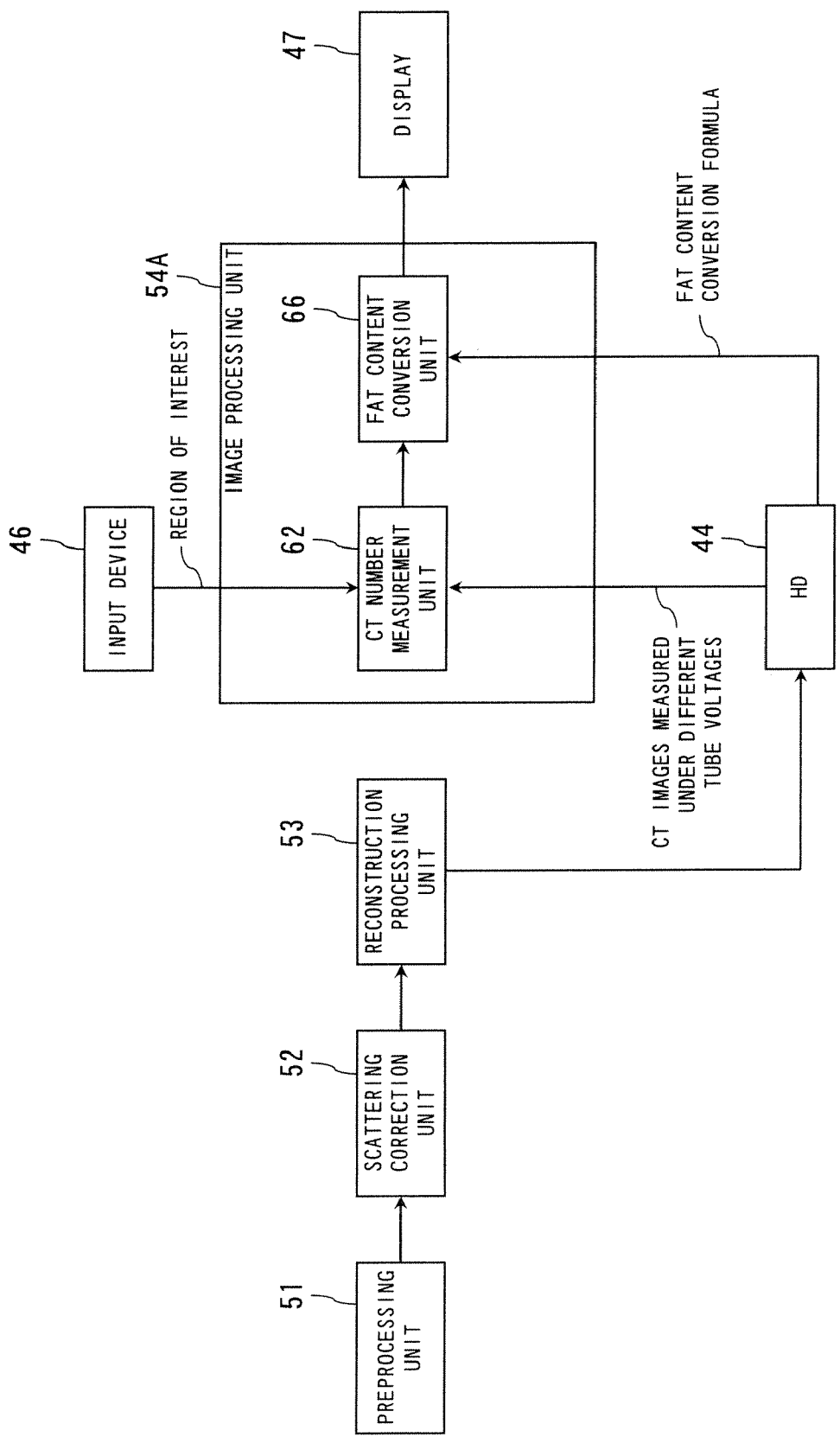
FIG. 10 is a block diagram showing a second embodiment of the X-ray CT apparatus according to the invention.

FIG. 10 is a block diagram showing the second embodiment of the X-ray CT apparatus according to the invention.

In the hardware architecture shown in FIG. 1, the CPU 41 of the operation console 4 of the X-ray CT apparatus 1 runs programs, whereby this operation console 4 functions as a preprocessing unit 51, a scattering correction unit 52, a reconstruction processing unit 53 and an image processing unit 54A.

The image processing unit 54A generates a display image in such a way that various items of image processing are executed for image data stored in the storage device such as HD 44. In order to generate the display image, the image processing unit 54A includes a CT number measurement unit 62 and a fat content conversion unit 66. By the way, in FIG. 10, members identical to those shown in FIG. 2 are assigned identical reference numerals, and they shall be omitted from description.

Here, a fat content conversion formula is previously stored in the storage device such as HD 44. More specifically, CT numbers under a plurality of different irradiation conditions are measured as sample CT numbers, with respect to fat contents, and the differences between the respectively corresponding sample CT numbers measured under the different irradiation conditions are evaluated. The fat content conversion formula indicates the relationship of the fat contents and the differences.

FIG. 11 is a diagram showing an outline for obtaining the fat content conversion formula. It is a diagram tabulating an example of the relationship of the sample CT numbers measured under the different irradiation conditions and the differences between the respectively corresponding sample CT numbers measured under the different irradiation conditions.

In order to obtain the fat content conversion formula at a preparatory stage before an examination, samples of various fat contents are first prepared, respectively. By way of example, the samples in which fats of weight-% values of 2%, 5%, 8%, 10%, 15% and 20% are mixed into water phantoms of predetermined quantity are respectively prepared. The table shown in FIG. 11 indicates as the sample CT numbers, the CT numbers which have been obtained in such a way that the samples of the various fat contents were measured under the different irradiation conditions, for example, tube voltages. By way of example, the sample CT number measured by irradiating the sample of the fat content of 2% under the tube voltage of 120 kV is defined as $^{102}C_{2\%}$, while the sample CT number measured by irradiating the same sample under the tube voltage of 80 kV is defined as $^{80}C_{2\%}$; the sample CT number measured by irradiating the sample of the fat content of 5% under the tube voltage of 120 kV is defined as $^{120}C_{5\%}$, while the sample CT number measured by irradiating the same sample under the tube voltage of 80 kV is defined as $^{80}C_{5\%}$; the sample CT number measured by irradiating the sample of the fat content of 8% under the tube voltage of 120 kV is defined as $^{120}C_{8\%}$, while the sample CT number measured by irradiating the same sample under the tube voltage of 80 kV is defined as $^{80}C_{8\%}$; the sample CT number measured by irradiating the sample of the fat content of 10% under the tube voltage of 120 kV is defined as $^{120}C_{10\%}$, while the sample CT number measured by irradiating the same sample under the tube voltage of 80 kV is defined as $^{80}C_{10\%}$; the sample CT number measured by irradiating the sample of the fat content of 15% under the tube voltage of 120 kV is defined as $^{120}C_{15\%}$, while the sample CT number measured by irradiating the same sample under the tube voltage of 80 kV is defined as $^{80}C_{15\%}$; and the sample CT number measured by irradiating the sample of the fat content of 20% under the tube voltage of 120 kV is defined as $^{120}C_{20\%}$, while the sample CT number measured by irradiating the same sample under the tube voltage of 80 kV is defined as $^{80}C_{20\%}$. Incidentally, although the case where the irradiation conditions are the tube voltages will be described below, the irradiation conditions are not restricted to the tube voltages, but they may well be, for example, tube currents (mA).

Besides, in the table shown in FIG. 11, the fat contents and the values of the differences between the sample CT numbers measured under the different tube voltages are respectively associated with each other. By way of example, the value η of the difference of the sample CT numbers as is calculated from ($^{120}C_{2\%}$–$^{80}C_{2\%}$) is associated with the sample whose fat content is 2%, the value θ of the difference of the sample CT numbers as is calculated from ($^{120}C_{5\%}$–$^{80}C_{5\%}$) is associated with the sample whose fat content is 5%, the value ι of the difference of the sample CT numbers as is calculated from ($^{120}C_{8\%}$–$^{80}C_{8\%}$) is associated with the sample whose fat content is 8%, the value κ of the difference of the sample CT numbers as is calculated from ($^{120}C_{10\%}$–$^{80}C_{10\%}$) is associated with the sample whose fat content is 10%, the value λ of the difference of the sample CT numbers as is calculated from ($^{120}C_{15\%}$–$^{82}C_{15\%}$) is associated with the sample whose fat content is 15%, and the value μ of the difference of the sample CT numbers as is calculated from ($^{120}C_{20\%}$–$^{80}C_{20\%}$) is associated with the sample whose fat content is 20%. By the way, in this embodiment, the different tube voltages were set at 120 kV and 80 kV as typical examples (tube currents were respectively held constant).

Besides, in order to obtain the fat content conversion formula, the relationship of the fat contents and the differences of the respectively corresponding sample CT numbers obtained under the different tube voltages is found on the basis of the table shown in FIG. 11.

Figure 12:
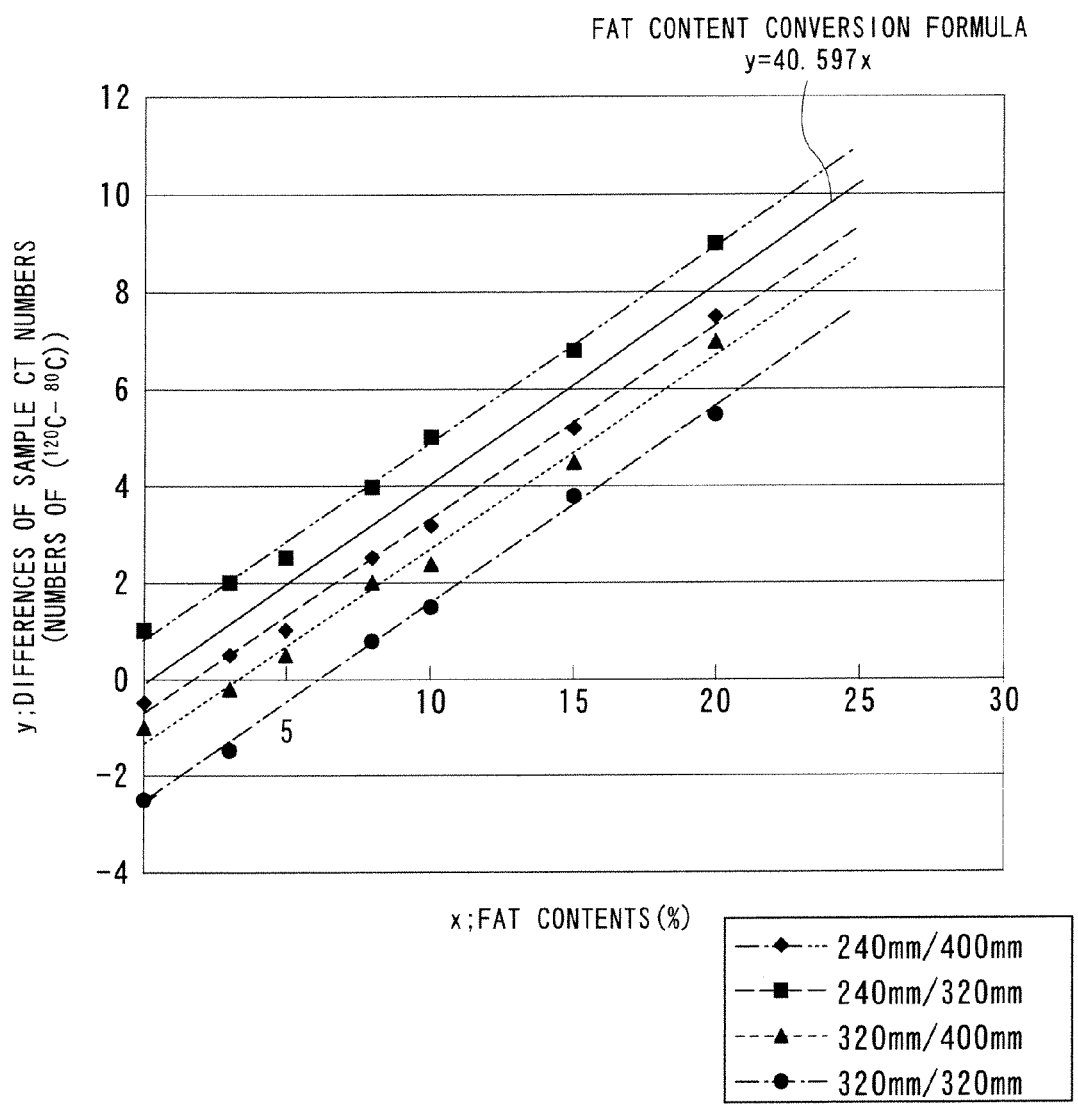
FIG. 12 is a diagram showing an example of a fat content conversion formula as a graph.

FIG. 12 is a diagram showing an example of the fat content conversion formula as graphs.

In FIG. 12, the relations between the fat contents (x) and the differences of sample CT numbers (y) are plotted for the respective combinations of the water-equivalent thicknesses of the patient P and FOVs, and regression lines based on the plots are indicated. Incidentally, the relations between the fat contents and the differences of the sample CT numbers were found for the respective combinations of the water-equivalent thicknesses of the patient P, the FOVs, and display FOVs in which scale-up ratios were considered. Then, it has been verified that the relations are approximately independent of the display FOVs.

The relations between the fat contents and the differences of the sample CT numbers are plotted under the condition that the combinations of the water-equivalent thicknesses of the patient P and the FOVs (water-equivalent thicknesses of the patient P/FOVs) are, for example, 240 mm/400 mm, 240 mm/320 mm, 320 mm/400 mm, and 320 mm/320 mm, and the regression lines based on the plots are respectively indicated as the graphs. As seen from the graphs, in all the combinations, the fat contents and the differences of the sample CT numbers assume positive correlations. Incidentally, the correlation coefficients among the regression lines exhibited 0.99 or above.

Besides, when measurement errors are considered, it cannot be said that gradients differed among the combinations, and the gradients substantially agreed irrespective of the combinations. Therefore, the straight line of y-intercept "0" whose gradient is the gradient of any of the regression lines or the mean of the gradients of the individual regression lines is set as the fat content conversion formula. Incidentally, here in FIG. 12, the straight line of the y-intercept "0" whose gradient is the mean (40.597) of the gradients of the individual regression lines is set as the fat content conversion formula, and the fat content conversion formula is indicated on a scatter diagram.

The fat content conversion unit 66 shown in FIG. 10 calculates the value of the difference between actually-measured CT numbers under different irradiation conditions, on the basis of the actually-measured CT numbers for the respective irradiation conditions as have been obtained by the CT number measurement unit 62. The difference is, for example, (actually-measured CT number at the tube voltage of 120 kV)−(actually-measured CT number at the tube voltage of 80 kV). Besides, the fat content conversion unit 66 converts the value of the difference between the actually-measured CT numbers, into the fat content by referring to the fat content conversion formula stored in the storage device. Further, the fat content converted by the fat content conversion unit 66 is displayed by the display 47, and it is quantified and displayed as the objective fat content of a predetermined region in a scano image.

Figure 13:
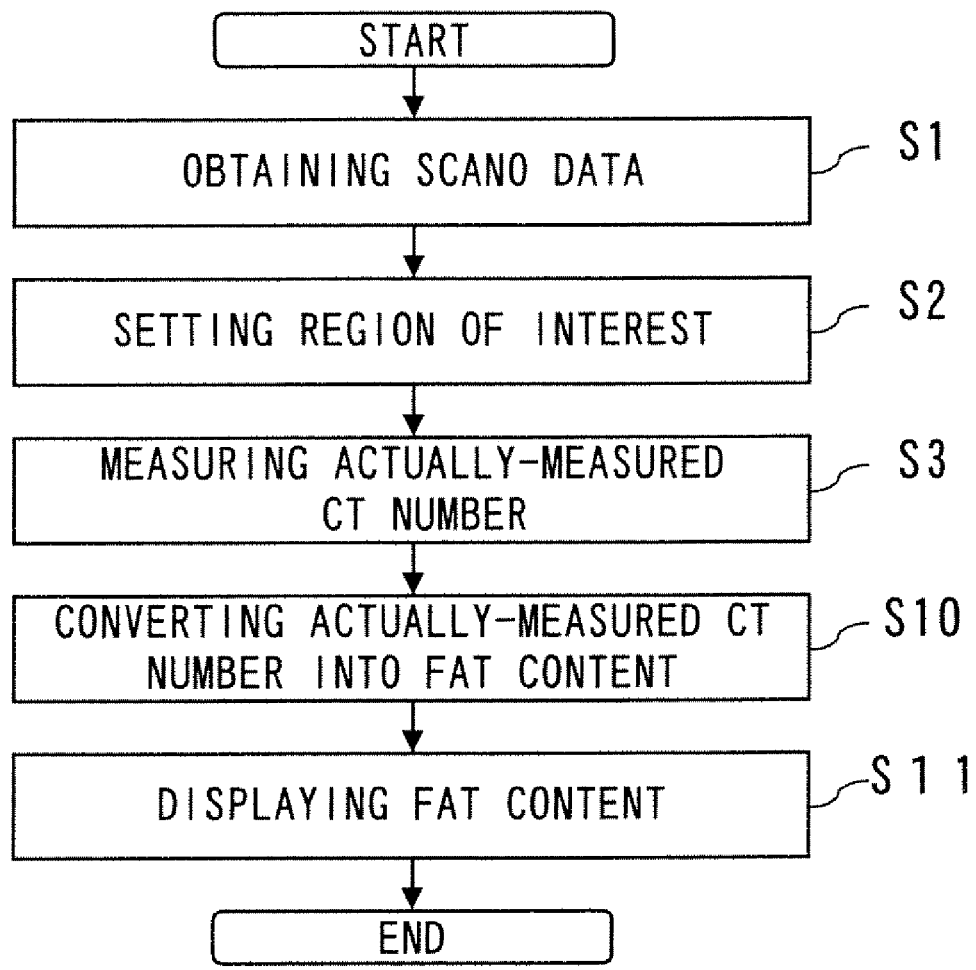
FIG. 13 is an operation of the second embodiment of the X-ray CT apparatus according to the invention will be described with reference to a flow chart.

Next, the operation of the image processing unit 54A in the second embodiment of the X-ray CT apparatus according to the invention will be described with reference to a flow chart shown in FIG. 13.

First, after a reconstruction process has been ended by the reconstruction processing unit 53 shown in FIG. 10, the image processing unit 54A obtains scano data from the storage device (step S1) and causes the display 47 to display the scano data as a scano image.

Subsequently, the diagnostician designates a predetermined region for the scano image displayed on the display 47, as described with reference to FIG. 7, whereby a region of interest is set (step S2).

Subsequently, the CT number measurement unit 62 obtains actually-measured CT numbers averaged for respective different irradiation conditions, as to the region of interest set at the step S2 (step S3), and it causes the display 47 to display CT images as shown in FIGS. 8 and 9.

Subsequently, the fat content conversion unit 66 converts the actually-measured CT numbers obtained by the CT number measurement unit 62, into a fat content by referring to a fat content conversion formula stored in the storage device (step S10).

The fat content converted by the fat content conversion unit 66 is displayed by the display 47 so that the diagnostician can visually recognize this fat content (step S11). By way of example, a character string "Fat content of pertinent region is - - - %" is indicated in superposition on the display of the CT image.

Incidentally, although the X-ray CT apparatus 1 is shown in FIG. 1 as an apparatus of single-tube type employing one X-ray tube 12, it may well be an apparatus of multi-tube type. In that case, individual X-ray tubes are set at different irradiation conditions, whereby CT numbers (sample CT numbers) under the different irradiation conditions can be obtained by one time of scan.

Incidentally, this embodiment is a mere example of the invention, and the invention shall not be restricted to the configurations and operations described in this embodiment. Various alterations are possible in accordance with a design, etc., within a scope not departing from the technical idea according to the invention.

In accordance with the image processing unit 54A of the X-ray CT apparatus 1 according to the invention, the fat content of the region of interest can be objectively quantified and displayed from the CT numbers which have been measured on the basis of the image information obtained by employing the X-ray CT apparatus 1.

What is claimed is:

1. An X-ray CT apparatus comprising:
    a first storage device configured to previously store therein a first table where a fat content and sample CT numbers for different irradiation conditions are associated with each other, the sample CT numbers having been obtained by irradiating water phantoms containing predetermined quantities of fats with X-rays under different irradiation conditions;
    a second storage device configured to previously store therein a second table of sample CT numbers for respective different water phantom sizes irradiated under different irradiation conditions;
    a CT number measurement unit configured to irradiate an object with X-rays under the different irradiation conditions, and to obtain actually-measured CT numbers for the different respective irradiation conditions;
    and a fat content obtaining unit configured to obtain a fat content corrected by a size of the object, based on the first table, the second table and the actually-measured CT numbers for the different respective irradiation conditions.

2. An X-ray CT apparatus according to claim 1, wherein the irradiation conditions are tube voltages of an X-ray tube.

3. An X-ray CT apparatus comprising:
    a first storage device configured to previously store therein a first table where a fat content and a ratio of sample CT numbers of desired water phantoms for different irradiation conditions are associated with each other, the sample CT numbers having been obtained in such a way that the water phantoms containing predetermined quantities of fats were irradiated with X-rays under the different irradiation conditions;
    a second storage device configured to previously store therein a second table where sample CT numbers at respective water-equivalent thicknesses of water phantoms of different sizes are stored for the different irradiation conditions;
    a CT number measurement unit configured to irradiate an object with X-rays under the different irradiation conditions, and to obtain actually-measured CT numbers for the different respective irradiation conditions;
    a size measurement unit configured to measure a water-equivalent thickness of the object;
    a size-dependent correction unit configured to calculate size-dependent correction coefficients based on the sizes of the desired water phantoms and the water-equivalent thickness of the object as has been measured by said size measurement unit, by referring to the second table, and to correct the actually-measured CT numbers by multiplying the actually-measured CT numbers by the size-dependent correction coefficients of the same irradiation conditions;
    a fat factor calculation unit configured to calculate a ratio of the actually-measured CT numbers corrected by said size-dependent correction unit, as a fat factor; and
    a fat content extraction unit configured to extract the fat content corresponding to the fat factor, by referring to the first table.

4. An X-ray CT apparatus according to claim 3, wherein the irradiation conditions are tube voltages of an X-ray tube.

5. An X-ray CT apparatus according to claim 3, wherein each of the size-dependent correction coefficients is obtained by a ratio of the sample CT number and the actually-measured CT number under the same irradiation condition.

6. An X-ray CT apparatus comprising:
a first storage device configured to previously store therein a first table where a fat content and a ratio of sample CT numbers for different irradiation conditions are associated with each other, the sample CT numbers being obtained by irradiating water phantoms containing predetermined quantities of fats with X-rays under the different irradiation conditions;
a second storage device configured to previously store therein a second table of CT numbers for respective different water phantom sizes irradiated under the different irradiation conditions;
a CT number measurement unit configured to irradiate an object with X-rays under the different irradiation conditions, and to obtain actually-measured CT numbers for the respective different irradiation conditions; and
a fat content obtaining unit configured to obtain a fat content corrected by a size of the object, based on the first table, the second table and the actually-measured CT numbers for the respective different irradiation conditions.

7. An X-ray CT apparatus according to claim 6, wherein the irradiation conditions are tube voltages of an X-ray tube.

8. An X-ray CT apparatus comprising:
a first storage device to previously store therein a first table where a fat content and a difference of sample CT numbers of desired water phantoms for different irradiation conditions are associated with each other, the sample CT numbers having been obtained in such a way that the water phantoms containing predetermined quantities of fats were irradiated with X-rays under the different irradiation conditions;
a second storage device to previously store therein a second table where sample CT numbers at respective water-equivalent thicknesses of water phantoms of different sizes are stored for the different irradiation conditions;
a CT number measurement unit configured to irradiate an object with X-rays under the different irradiation conditions, and to obtain actually-measured CT numbers for the different respective irradiation conditions;
a size measurement unit configured to measure a water-equivalent thickness of the object;
a size-dependent correction unit configured to calculate size-dependent correction coefficients based on the sizes of the desired water phantoms and the water-equivalent thickness of the object as has been measured by said size measurement unit, by referring to the second table, and to correct the actually-measured CT numbers by multiplying the actually-measured CT numbers by the size-dependent correction coefficients of the same irradiation conditions;
a fat factor calculation unit configured to calculate a difference of the actually-measured CT numbers corrected by said size-dependent correction unit, as a fat factor; and
a fat content extraction unit configured to extract the fat content corresponding to the fat factor, by referring to the first table.

9. An X-ray CT apparatus according to claim 8, wherein the irradiation conditions are tube voltages of an X-ray tube.

10. An X-ray CT apparatus according to claim 8, wherein each of the size-dependent correction coefficients is obtained by a difference of the sample CT number and the actually-measured CT number under the same irradiation condition.

11. An X-ray CT apparatus comprising:
a storage device which stores therein a conversion formula that has been calculated on the basis of fat contents versus values of differences of CT numbers;
a CT number measurement unit which irradiates an object with X-rays under different irradiation conditions, and which obtains actually-measured CT numbers for the different irradiation conditions; and
a fat content conversion unit which calculates the difference of the actually-measured CT numbers for the respective irradiation conditions, and which converts the difference of the actually-measured CT numbers into the fat content, by referring to the conversion formula.

12. An X-ray CT apparatus according to claim 11, wherein the irradiation conditions are tube voltages of an X-ray tube.

13. An X-ray CT apparatus according to claim 11, wherein relations between the fat contents and differences of sample CT numbers between the plurality of different irradiation conditions of desired water phantoms are plotted, the relations having been obtained in such a way that the water phantoms containing predetermined quantities of fats were irradiated with X-rays under the respective irradiation conditions in respective combinations of water-equivalent thicknesses of the object and fields of view, and
regression lines in the respective combinations as are based on the plots are used for calculating the conversion formula.

* * * * *